United States Patent [19]

Ruggiu et al.

[11] Patent Number: 5,411,862
[45] Date of Patent: May 2, 1995

[54] METHOD FOR THE RAPID SEQUENCING OF LINEAR AND ORDERED BIOLOGICAL SEQUENCES

[75] Inventors: Gilles Ruggiu, Orsay; Frédéric Ginot, Versailles, both of France

[73] Assignee: Bertin & Cie, France

[21] Appl. No.: 30,411

[22] Filed: Apr. 23, 1993

[30] Foreign Application Priority Data

Sep. 28, 1990 [FR] France .................. 90 11977

[51] Int. Cl.⁶ .................................. C12Q 1/68
[52] U.S. Cl. ................................ 435/6; 435/91.1
[58] Field of Search ................ 435/6, 91, 91.1

[56] References Cited

PUBLICATIONS

Pearl, Bayesian Decision Methods, in "Encyclopedia of Artificial Intelligence", vol. 1, Ed. by Shapiro et al., New York: John Wiley & Sons, 1990, pp. 48–56.
Proceedings of the National Academy of Sciences of the USA vol. 26 No. 5, May 1979, M. O. Dayhoff et al. "Methods for Identifying Proteins by Using Partial Sequences" pp. 2170–2174.
Japanese Patents Gazette, Section Ch: Chemical, Jul. 13, 1988, Derwent Publctns Ltd. (London), week 8822, "Estimating Amino Acid Sequence of Peptide-by adding given number of amino acids to peptide terminal & calculating probability of acid sequence ..." Abstract J6 3091-564A, p. 14.
Int'l Search Report of PCT/FR91/00746 by EPO dated Dec. 13, 1991.

*Primary Examiner*—Margaret Parr
*Assistant Examiner*—Scott W. Houtteman
*Attorney, Agent, or Firm*—Vickers, Daniels & Young

[57] ABSTRACT

Improved method for rapidly sequencing elements constituting a linear or linearized and ordered biological sequence such as a DNA fragment is provided. The method consists of extracting purifying and where appropriate fragmenting and/or amplifying a biological sequence in order to obtain a plurality of identical sequences which are subsequently combined to identify the complete DNA fragment.

5 Claims, 2 Drawing Sheets

METHOD FOR THE RAPID SEQUENCING OF LINEAR AND ORDERED BIOLOGICAL SEQUENCES

The present invention relates to a method for the rapid sequencing of linear and/or previously linearized and ordered biological sequences, in particular of proteins and nucleic acids.

THE BACKGROUND OF THE INVENTION

The present invention is particularly applicable to a method for rapidly sequencing linear and/or previously linearized and ordered biological sequences and it will be discussed with particularly reference thereto. However, the invention has broader applications which will become apparent upon the reading of the specification in conjunction with the drawings.

The current methods of determination of both proteins and nucleic acids are arduous to carry out.

For the determination of proteins, the Edman method may be mentioned in particular.

For determination of the sequence of a nucleic acid, there are broadly two major types of method at the present time: chemical methods and enzymatic methods.

The chemical method, represented essentially by the Maxam and Gilbert method, is based on obtaining fragments whose size enables the position of one of the four bases to be defined. Before any determination, the DNA is purified in single-stranded form and then labelled at one of its ends with $^{32}P$. It is then separated into four subsets, which each undergo a different chemical treatment which alters one type of base in an absolutely specific manner (modification of the base, removal of the modified base and cutting of the strand at the sugar residue) and brings about cleavage of the said sequence into two fragments. The chemical parameters are chosen in such a way that each fragment has on average a single base modified and then removed. After cleavage, each subset hence contains a population of labelled fragments of variable size, all having the same end and terminating in the same type of base in the sequence.

After electrophoretic separation and visualization by autoradiography, the length of the segment observed is equal to the distance between the point of cutting and the point of labelling. Since the resolution of the polyacrylamide gels used is one base, the linkage of the fragments on the autoradiogram corresponds to the linkage of the bases in the DNA fragment.

Reading is direct, and a sequence of 100 to 400 bases may be read on a single gel.

This method is best suited to fragments of the order of 500 bp, present in fairly large amounts and for which the secondary structures are significant.

The enzymatic method, essentially represented by the Sanger method, consists in synthesizing with a suitable enzyme (polymerase or reverse transcriptase) the strand complementary to the strand which it is desired to sequence and which must be integrated in a single- or double-stranded vector capable of replicating.

The synthesis of the second strand is accomplished in the presence of the 4 deoxyribonucleotides (dATP, dCTP, dTTP, dGTP), at least one of which must be radioactively labelled, and of a primer which will hybridize with a region immediately upstream of the fragment to be sequenced.

The principle of this technique consists in adding a different specific dideoxynucleotide (ddATP, ddCTP, ddTTP or ddGTP) into four reaction tubes. These ddNTPs may be incorporated in the chain undergoing elongation but not possessing a hydroxyl group at the 3'; their incorporation stops the elongation of the strand. Each reaction tube hence contains, at the end of the reaction, a population of fragments of variable size, all having the same 5' end and terminating in the same dideoxynucleotide (ddNTP). The size of the fragments synthesized, and hence the size of the fragments detectable by autoradiography after electrophoresis, is equal to the distance between the beginning of the primer and the base at which replication has stopped.

It is possible by this technique to determine sequences of 300 to 800 bases, depending on the lengths and the quality of the polyacrylamide gels used for the separation.

Other methods have been proposed to enable the steps of subcloning to be reduced (sequencing of the double-stranded fragment, use of PCR, shot-gun sequencing, for example).

The shot-gun method, in particular, consists in cloning fragments of the gene to be sequenced at random in M13 without having any information about their organization in the genome.

The fragments are then sequenced and their organization is worked out by cross-checking using a computer; however, this method necessitates the direct sequencing of at least 20% of the sequences which it has not been possible to position by cross-checking.

In view of the difficulty of obtaining the missing sequences, more efficacious adaptations have been developed; brief mention may be made of the method of sequencing by cloning and enzymatic deletions, and the method of sequencing by transposon-induced deletions.

However, all these methods are arduous to carry out.

International Application PCT WO 89/03432 describes, for its part, a method of rapid sequencing of DNA and RNA, in which a single-stranded DNA or RNA fragment, bound where appropriate to a solid support, is placed in a flowing liquid and is cleaved with an exonuclease, starting from one of its ends, so as to form a succession of bases in the flowing sample. The bases are then detected during their sequential passage through a detector, to reconstruct the base sequence of the said DNA or RNA fragment to be determined. In a particular embodiment, the strand complementary to the sequence to be determined is synthesized in the presence of modified nucleotides each possessing a specific characteristic (different fluorescence). The synthesized fragment is then placed on a solid support in the flowing liquid sample and the different nucleotides which are identifiable are cleaved sequentially and detected.

However, in such a method, not all of the bases can, in fact, be labelled, in particular for reasons of steric hindrance.

THE SUMMARY OF THE INVENTION

The subject of the invention is a method for the sequencing of linear or linearized and ordered biological sequences which meets the practical requirements better than the methods of the prior art, in particular by enabling the complete sequence to be obtained much more rapidly than in the methods previously described, starting from partially labelled fragments.

The invention proposes, to this end, a method for sequencing the elements constituting a linear or linearized and ordered biological sequence, the method consisting, in particular, in extracting, purifying and, where appropriate, fragmenting and/or amplifying a biological sequence in order to obtain a plurality of identical sequences, in combining suitable specific labels with the elements of these sequences, and then in identifying sequentially and counting the labels combined with the said elements in order to deduce therefrom a complete sequence of elements, characterized in that it consists in:
  labelling the said sequences with the set of specific labels mentioned above, the efficiency of the labelling being less than 100%,
  detecting and identifying sequentially the labels combined with the elements in the said sequences, so as to obtain lacunar or incomplete sequences of labelled elements, which sequences differ from one another in respect of the labelled elements, each of which sequences comprises a number of labelled elements lower than the number N of elements constituting the said complete sequence, and in each of which sequences the spaces between labelled elements have unknown lengths, and
  reconstituting the ordered succession of elements constituting the complete sequence, by calculating from the said lacunar sequences the probabilities of presence of the elements in the complete sequence, and by selecting the elements whose probabilities of presence are close to 1 or equal to 1 while the probabilities of presence of the other elements are close to 0 or equal to 0.

Linear or linearized biological sequence, in the sense used in the present-invention, is understood to mean both proteins, the elements of which are the natural amino acids, and nucleic acids (DNA and RNA), the elements of which are the bases or nucleotides: adenine, cytosine, guanine, thymidine, designated by the letters A, C, G and T, for DNA, and A, C, G and U (uracil) for RNA. For reasons of simplicity, in the text below, RNA will be designated by the same letters as DNA.

According to another feature of the invention, this method also consists in calculating the probabilities of presence of the elements in the complete sequence, starting from predetermined initial values of these probabilities and taking into account the labelled elements present in a first lacunar sequence, and then in modifying the probabilities thereby obtained by taking into account the labelled elements present in a second lacunar sequence, and so on, until probabilities equal to 1 or close to 1 are arrived at for each element of the complete sequence.

According to yet another feature of the invention, the method consists, in addition, in performing the abovementioned calculations proceeding element by element and position by position of the complete sequence, calculating the probability of presence of each possible element for a given position, and then the probability of presence of each possible element for the next position in the complete sequence, and so on.

This procedure simplifies the calculations and greatly reduces the processing time on a computer or microcomputer.

The probability of presence of an element Bj at a position i in the complete sequence is then given by the following formula:

$$P_p^i(Bj) = \frac{P_{p-1}^i(Bj) \cdot P(S_p/Bj)}{\sum_{j=1}^{4} P_{p-1}^i(Bj) \cdot P(S_p/Bj)},$$

$P_p^i(Bj)$ being the probability of the presence of the element Bj at position i of the complete sequence after consideration of p lacunar sequences,
$P_{p-1}^i(Bj)$ being the probability of the presence of the element Bj at position i of the complete sequence after consideration of (p−1) lacunar sequences,
$P(S_p/Bj)$ being the probability of the lacunar sequence $S_p$, knowing the element Bj at position i.

According to another advantageous feature of the invention, the method consists in determining beforehand the number N of elements of the complete sequence.

According to yet another advantageous feature of the invention, the method consists in determining beforehand, for each type of element, the total number of elements of this type in the complete sequence, independently of their position in the sequence.

According to an advantageous arrangement of the invention, the number of elements of each type in the complete sequence is determined chemically.

It is thus possible to begin the calculation of the probabilities from the number of elements of each type in the complete sequence, the initial value of the probability of an element Bj at a position being equal to nj/N, nj being the total number of elements Bj in the complete sequence and N being the total number of elements in this sequence.

So that the calculation may be performed fairly rapidly, the number N is chosen, for example, to be between 10 and 30 approximately.

In the case of a biological sequence which comprises a large number of elements, complete sequences of N elements which mutually overlap at the ends are considered, N being between 10 and 30 approximately, and the successions of elements constituting these successive sequences are determined in the abovementioned manner, thereby enabling the complete biological sequence under consideration to be reconstituted.

A better understanding of the invention will be gained, and other features, details and advantages thereof will become more clearly apparent, on reading the description which follows.

DESCRIPTION OF THE PREFERRED EMBODIMENT

Figure 1A:
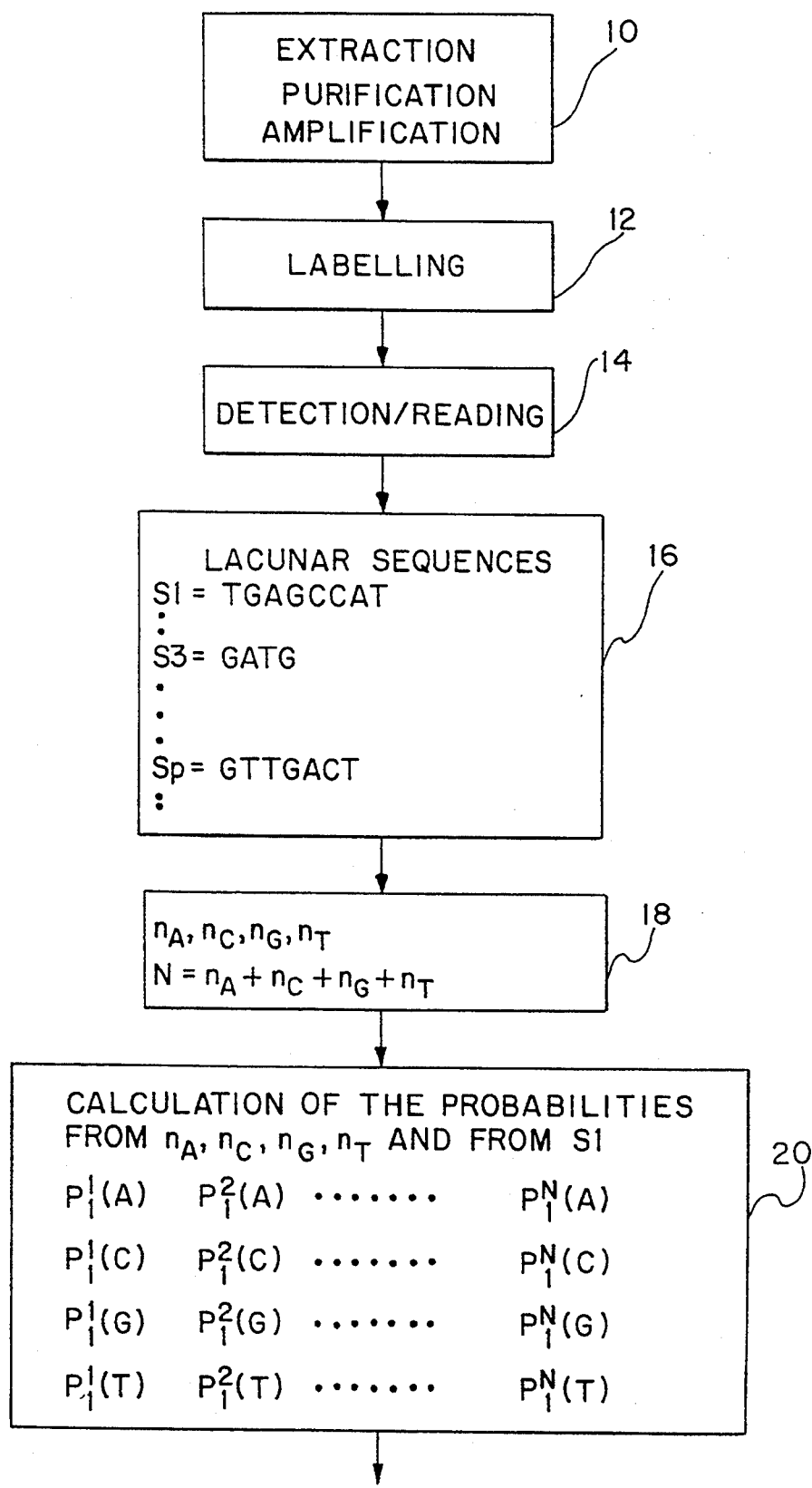
FIGS. 1A and 1B are a graphic illustration of a process flow chart illustrating the biological sequencing process according to the present invention.
Figure 1B:
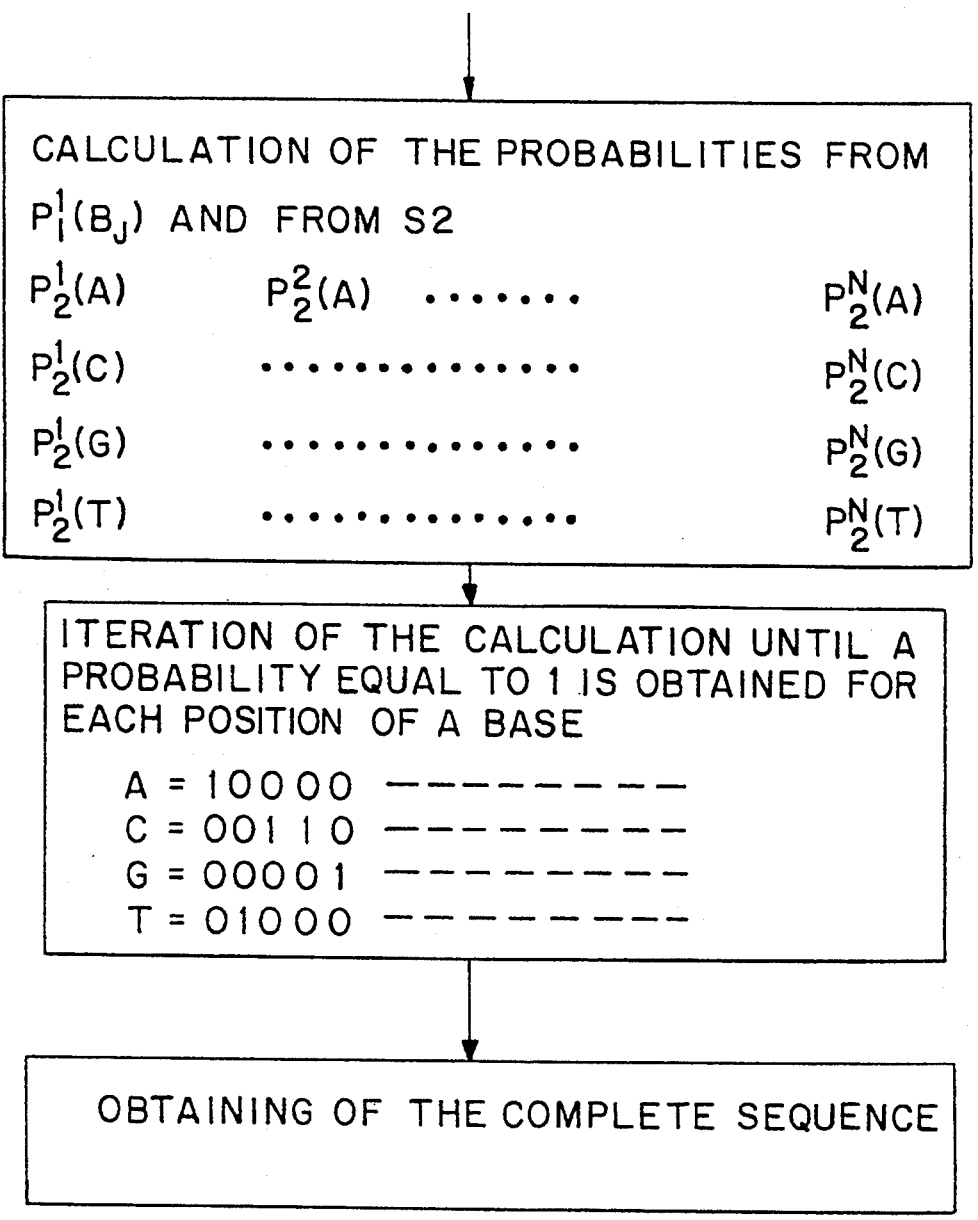

Referring now to the drawings, wherein the showings are for the purpose of illustrating the preferred embodiments of the invention only and not for the purpose of limiting the same, a first step of the method, designated by reference 10 in FIG. 1A, consists conventionally in extracting and purifying a nucleic acid fragment and, where appropriate, in amplifying it when it is present in very small amounts, for example by the PCR method.

The second step of the method, designated by reference 12, consists in combining specific labels with the bases of the nucleic acid fragments, which labels, for reasons of steric hindrance, may not be combined with all the bases of these fragments.

It is possible, in a known manner, to make copies of the DNA fragments using a suitable polymerase, in the presence of the nucleotides A, C, G and T and of analogues of the nucleotides specifically labelled with different fluorochromes, hereinafter designated a, c, g and t: a specifically labels adenine, c specifically labels cytosine, g specifically labels guanine and t specifically labels thymidine.

A set of DNA fragments which are partially and differently labelled is thereby obtained, the labelled bases not being the same in the different fragments, and the numbers of labelled bases also differing from one element to another.

The next step of the process, designated by reference 14, consists in detecting or reading the labelled bases. For this purpose, it is possible to spread the different DNA fragments on a microscope slide, and to detect the labels combined with bases, for example by means of a tunnelling microscope or by conoscopic holography.

A set of lacunar sequences S1, S2, S3 ..., Sp, ..., of labelled bases is thereby obtained, as shown at 16, in which one lacunar sequence will differ from another in respect of the number of labelled bases, the positions of the labelled bases and the spaces between labelled bases.

According to the invention, knowledge of this set of lacunar or incomplete sequences of labelled bases makes it possible to get back to the complete sequence of bases constituting the nucleic acid fragment under study.

For this purpose, the probability of presence of each possible base A, C, G or T at each position i of a base in the complete sequence will be calculated from the information contained in the abovementioned lacunar sequences, which are incomplete but ordered successions of labelled bases. Theoretically, BAYES's formula enables the probability of any combination Ck of N elements to be calculated knowing a set S of partial successions of elements drawn from a particular combination:

$$P(Ck/S) = \frac{P(Ck) \cdot P(S/Ck)}{\sum_k P(Ck) \cdot P(S/Ck)}$$

with $P(Ck/S)$ = probability of any combination Ck knowing S
$P(Ck)$ = probability of a combination Ck
$P(S/Ck)$ = probability of S knowing Ck Application of this formula in the present case is virtually impossible as a result of the volume of calculations to be performed: in effect, if a sequence of N bases is considered, the number of combinations Ck is equal to $4^N$, that is to say is greater than $10^6$ when N is greater than 10.

The invention hence provides for simplification of these calculations, in order to reduce considerably the time they take on a data processing system, by proceeding, for example, in the following manner:

the calculations are performed considering each lacunar sequence S1, S2, ..., Sp, ... one after the other instead of considering the set S of these lacunar sequences, instead of calculating the probability of a possible sequence of N bases, the probability of each possible base at each base position of the nucleic acid fragment under consideration is calculated.

These two simplifications make it possible to arrive at the following formula:

$$P_p^i(Bj) = \frac{P_{p-1}^i(Bj) \cdot P(Sp/B)}{\sum_{j=1}^{4} P_{p-1}^i(Bj) \cdot P(Sp/Bj)},$$

with $P_p^i(Bj)$ = equals probability of the base Bj at position i of the complete sequence after consideration of the first p lacunar sequences $P_{p-1}^i(Bj)$ = probability of the base Bj at position i of the complete sequence after consideration of the first (p − 1) lacunar sequences $P(Sp/Bj)$ = probability of the lacunar sequence Sp knowing the base Bj at position i of the complete sequence $Bj$ = A, C, G or T.

Such a calculation may be carried out without difficulty on a microcomputer for values of N between 10 and 30 approximately, N being the number of bases of the desired complete sequence.

This calculation may be begun by considering that all the bases have equal probabilities ($\frac{1}{4}$) of occurring at a given position of the sequence.

It is, however, more advantageous to begin the calculation starting from probabilities which are closer to reality. For this purpose, it is possible to determine, for example by a chemical method, the numbers $n_A$, $n_C$, $n_G$, $n_T$ and the total number of N bases A, C, G, T in the sequence under study.

This step is designated by the reference 18 in FIG. 1A.

The next step of the process, carried out on a microcomputer for example, consists in applying the abovementioned formula.

As shown at 20 in FIG. 1A, the probabilities of presence of each possible base at each position of the complete sequence are hence calculated from the numbers of bases of each type $n_A$, $n_C$, $n_G$, $n_T$ and from the first lacunar sequence S1. The results of this calculation may be presented in the form of a table or matrix of values, in which the first line shows the probabilities of presence of the base A at the various positions of bases in the complete sequence, the second line shows the probabilities of presence of the base C at the various positions of the complete sequence, the third line shows the probabilities of presence of the base G at the various positions of this complete sequence and the fourth line shows the probabilities of presence of the base T at the various positions of the complete sequence.

By successive iterations and considering successively the lacunar sequences S2, ..., Sp, ..., a table is arrived at which will be composed only of 1 and 0 (or of figures very close to 1 and figures very close to 0), the 1's identifying the bases present at the various positions in the complete sequence, and the 0's confirming that other bases do not occur at these same positions.

The abovementioned lacunar sequences may naturally be considered in any order. It is, however, more advantageous to consider them in decreasing order of number of labelled bases, in order to benefit from a maximum amount of information from the very beginning of the calculations.

It is also advantageous, after performing the calculations corresponding to a certain number of lacunar sequences, to continue these calculations by dealing with the lacunar sequences richest in information.

This results in a reduction in the calculation time which can be relatively large.

The number of lacunar sequences to be considered for reconstitution of a complete sequence varies with the efficiency of labelling of the bases of this complete sequence. For an efficiency of labelling of the order of 30%, around twenty indifferently chosen lacunar sequences should be considered, it being possible for this number to be reduced if the lacunar sequences richest in information are selected. The time taken for the calculations on a standard type microcomputer can vary from a few minutes, to a few tens of minutes, depending on the case.

The complete sequences studied can be of any length. If the method according to the invention is carried out using a microcomputer, it will be advantageous to limit this number to approximately 30. In the case where relatively long sequences of bases are studied, it suffices to break these complete sequences down into successive sequences of 20 to 30 bases approximately which overlap at their ends, and to determine the constitution of these successive sequences.

Generally speaking, the invention is applicable every time a linear and ordered biological sequence has to be reconstituted from ordered but incomplete information. It hence applies both to the sequencing of nucleic acids and to that of proteins.

As emerges from the foregoing, the invention is in no way limited to those of its embodiments, implementations and applications which have just been described more explicitly; it encompasses, on the contrary, all variants which may occur to the specialist in the field, without departing from the scope or the range of the present invention.

Having defined the invention, the following is claimed:

1. A method for determining the complete sequence of N bases of a nucleic acid fragment comprising:

extracting nucleic acid and purifying a nucleic acid fragment;

synthesizing copies of said fragment in the presence of all four nucleic acid bases and all four nucleic acid bases wherein each base is modified by the addition of a different detectable label to obtain a plurality of labelled copies; wherein said copies are partially and differentially labeled;

detecting the labelled bases in each copy and determining the sequence of said labelled bases to form a set of p lacunar sequences $S_1, S_2, S_3, \ldots S_p$ of labelled bases;

determining the complete sequence from said lacunar sequences by calculating the probability of presence of a base Bj, j being a number from one to four wherein each number represents a particular nucleic acid base, at a position i in the complete sequence wherein:

$$P_p^i(Bj) = \frac{P_{p-1}^i(Bj) \cdot P(S_p/Bj)}{\sum_{j=1}^{4} P_{p-1}^i(Bj) \cdot P(S_p/Bj)}$$

$P_p^i(Bj)$ being the probability of the presence of the base Bj at position i of the complete sequence after consideration of p lacunar sequences, $P_{p-1}^i(Bj)$ being the probability of the presence of the base Bj at position i of the complete sequence after consideration of (p−1) lacunar sequences, $P(S_p/Bj)$ being the probability of said lacunar sequence $S_p$, knowing the base Bj at position i in said complete sequence, repeating the process until, at each position of said complete sequence, probabilities of about 1 are arrived at for one of the four bases;

wherein the complete sequence of N bases is the sequence of bases at each position which have the probabilities of about 1.

2. A method according to claim 1, wherein said synthesis is by the polymerase chain reaction.

3. A method according to claim 1, wherein before said lacunar sequences are determined, the total number of bases of said complete sequence is determined, the numbers of bases of each type in said complete sequence are determined and the initial value of the probability of the presence of a base Bj at a given position i is equal to nj/N wherein nj is the total number of said bases Bj in the complete sequence and N is the total number of said bases in said complete sequence.

4. A sequencing method according to claim 1, wherein N is about 10 to 30 bases.

5. A sequencing method according to claim 1, wherein when the number N of bases of the complete sequence is greater than 30, said method comprises: breaking down of said complete sequence into successive sequences of about 10 to 30 bases, said successive sequences overlapping at their ends, determining the base sequence of each successive sequence according to the claimed method, and reconstituting the successive sequences to form the complete sequence.

* * * * *